(12) United States Patent
Zambaux

(10) Patent No.: US 9,079,319 B2
(45) Date of Patent: Jul. 14, 2015

(54) DISPOSABLE PRODUCTION LINE

(75) Inventor: Jean-Pascal Zambaux, Audenge (FR)

(73) Assignee: PALL LIFE SCIENCES BELGIUM, Hoegaarden (BE)

( * ) Notice: Subject to any disclaimer, the term of this patent is extended or adjusted under 35 U.S.C. 154(b) by 96 days.

(21) Appl. No.: 13/516,153

(22) PCT Filed: Dec. 20, 2010

(86) PCT No.: PCT/EP2010/070284
§ 371 (c)(1),
(2), (4) Date: Jun. 14, 2012

(87) PCT Pub. No.: WO2011/076758
PCT Pub. Date: Jun. 30, 2011

(65) Prior Publication Data
US 2012/0294697 A1    Nov. 22, 2012

(30) Foreign Application Priority Data

Dec. 21, 2009  (FR) .................................... 09 306300

(51) Int. Cl.
*B01L 99/00*   (2010.01)
*B25J 21/02*   (2006.01)
(Continued)

(52) U.S. Cl.
CPC .............. *B25J 21/02* (2013.01); *B08B 15/023* (2013.01); *C12M 37/00* (2013.01); *Y10T 29/49826* (2015.01)

(58) Field of Classification Search
CPC .................................................. B08B 15/023
USPC ....................................................... 422/567
See application file for complete search history.

(56) References Cited

U.S. PATENT DOCUMENTS 4,170,421 A * 10/1979 Balding et al. ................ 366/144
5,219,215 A    6/1993 Akagawa et al.
(Continued)

FOREIGN PATENT DOCUMENTS

DE    4030186    4/1991
EP    1264668    12/2002
(Continued)

OTHER PUBLICATIONS

Partial European Search Report EP 14 18 9523 Mar. 17, 2015.

*Primary Examiner* — Jill Warden
*Assistant Examiner* — Brittany Fisher
(74) *Attorney, Agent, or Firm* — King & Schickli, PLLC

(57) ABSTRACT

The invention relates to a disposable production line. The invention relates notably to a process for manipulating, manufacturing or packaging products or devices under inert atmosphere, and/or sterile conditions and/or pyrogen free environment.
In particular the invention relates to a closed disposable equipment comprising at least two separate disposable isolators including a first disposable isolator and a last disposable isolator, wherein said separate disposable isolator is connected to at least one other separate disposable isolator by at least one connecting means, wherein each separate disposable isolator comprises a working place, said working place being located inside said separate disposable isolator, said working place being under inert atmosphere, and/or disinfected, and/or sterile and/or pyrogen free conditions, said working place enabling the manipulation of containers, products or devices, wherein said closed disposable equipment comprises at least one inlet for introducing containers, products or devices into said closed disposable equipment and at least one outlet for discharging said containers, products or devices from said closed disposable equipment.

18 Claims, 3 Drawing Sheets

(51) Int. Cl.
 *C12M 1/12* (2006.01)
 *B08B 15/02* (2006.01)

(56) References Cited

U.S. PATENT DOCUMENTS

| | | | |
|---|---|---|---|
| 5,476,635 A * | 12/1995 | Stoker | 422/26 |
| 5,881,535 A | 3/1999 | Gliniecki et al. | |
| 5,890,781 A | 4/1999 | Ryder | |
| 6,651,404 B1 | 11/2003 | Hertfelder | |
| 8,298,054 B2 | 10/2012 | Hodge et al. | |
| 2002/0043273 A1 | 4/2002 | Chau | |
| 2002/0179602 A1 * | 12/2002 | Cocker et al. | 220/6 |
| 2003/0137225 A1 | 7/2003 | Hauville | |
| 2004/0215362 A1 * | 10/2004 | Kokubo et al. | 700/130 |
| 2005/0232807 A1 * | 10/2005 | Nishimura | 422/1 |
| 2008/0141622 A1 * | 6/2008 | Bechini | 53/167 |
| 2008/0240981 A1 * | 10/2008 | Berentsveig et al. | 422/29 |
| 2010/0107567 A1 | 5/2010 | Khan et al. | |
| 2010/0253071 A1 * | 10/2010 | Lloyd | 285/236 |
| 2013/0017131 A1 | 1/2013 | Galliher et al. | |

FOREIGN PATENT DOCUMENTS

| | | |
|---|---|---|
| FR | 2155816 A1 | 5/1973 |
| FR | 2293769 | 7/1976 |
| GB | 1528478 | 10/1978 |
| JP | H0342599 U | 4/1991 |
| JP | H05157302 A | 6/1993 |
| JP | 2008232541 A | 10/2008 |
| WO | 2004114378 A1 | 12/2004 |
| WO | WO 2007/019568 | 2/2007 |

* cited by examiner

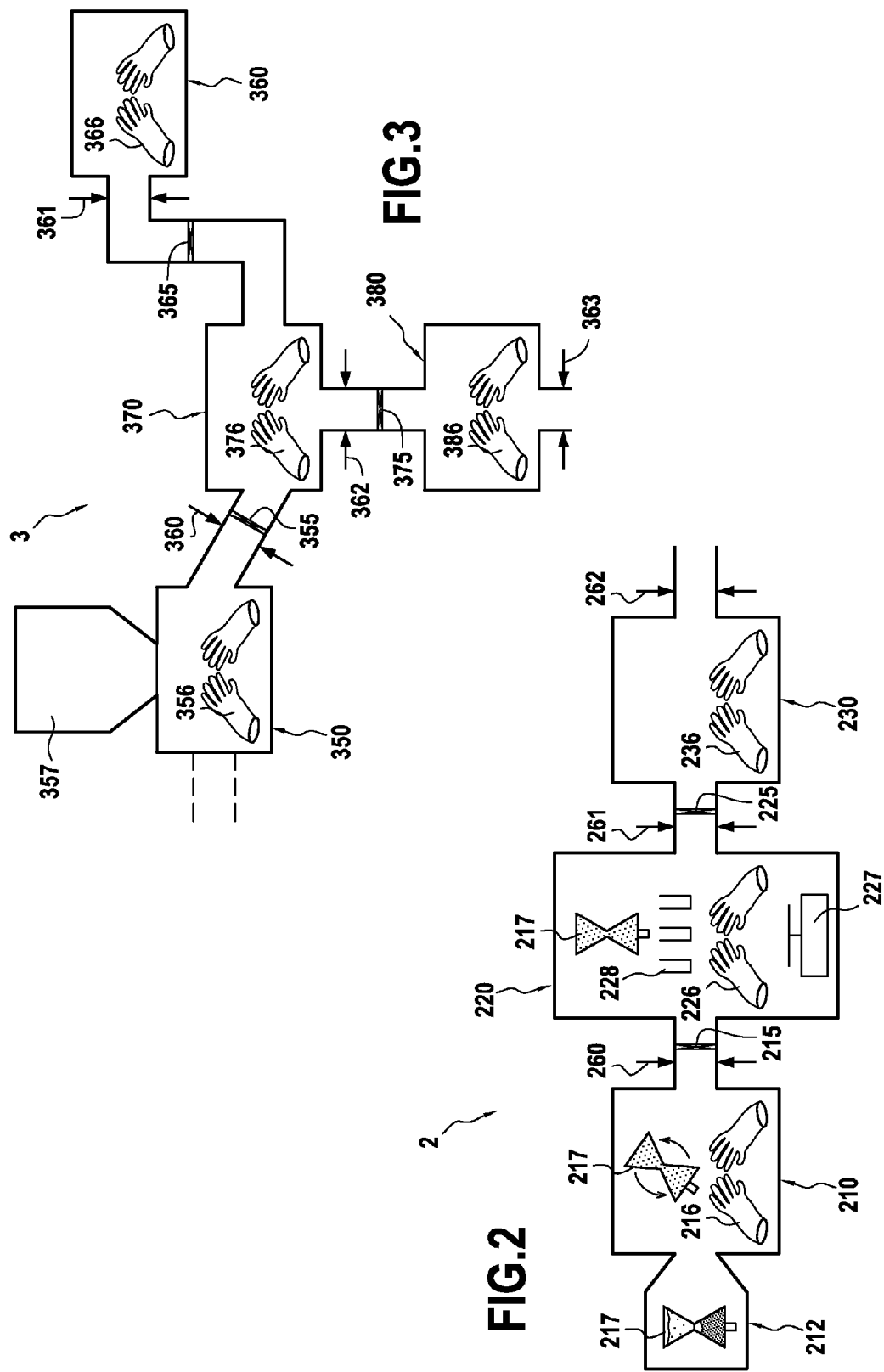

DISPOSABLE PRODUCTION LINE

The invention relates mainly to a disposable production line. The invention relates notably to a process for manipulating, manufacturing or packaging products or devices under inert atmosphere, and/or sterile conditions and/or pyrogen free environment.

STATE OF THE ART

The art, notably in the medical, chemical, biochemical or pharmaceutical field, describes devices for manufacturing or packaging products under inert atmosphere, and/or sterile conditions and/or pyrogen free environment.

The skilled person preparing medicament or active pharmaceutical ingredients (API) is used to prepare products under inert atmosphere, and/or sterile conditions and/or pyrogen free environment. However the existing equipments need to be prepared before use when inert atmosphere or sterile conditions or pyrogen free environment are needed. Often this means that the whole equipment should be treated, physically or chemically, to inert the atmosphere or to be the sterile or depyrogenated (pyrogen free) before use. Since several years, there is a need of providing disposable working places or chambers and in particular of disposable devices or disposable isolators, notably to satisfy the existing need of working under inert atmosphere, and/or sterile conditions and/or pyrogen free environment.

Known systems allow a skilled person to handle materials inside a working chamber. Such systems may be operated from the exterior by handling the products inside the confined atmosphere using gloves integrated to the system. When needed, the whole work or manufacture should be done in a sterile room or a room where the atmosphere is inert. Of course this implies costs because it needs special techniques and procedures for sterilising both materials and equipments, and skilled persons.

Nowadays the process for manufacturing products that requires inert or sterile or pyrogen free manufacturing conditions is still not satisfactory.

GOAL OF THE INVENTION

The present invention aims mainly to provide a disposable production line which may be qualified for manipulating, handling, manufacturing, or packaging products or devices needing regulations and/or approval by Competent Authorities such as for pharmaceutical compounds, biohazardous compounds, anti-cancer or anti-viral drugs, medical devices, pre-filled syringes, prosthesis, etc.

The present invention aims mainly to provide a disposable production line for manipulating, handling, manufacturing, or packaging products or devices under inert atmosphere, and/or sterile conditions and/or pyrogen free environment, such as for pharmaceutical compounds, biohazardous compounds, anti-cancer or anti-viral drugs, medical devices, electronic devices, etc.

The invention aims to provide a process for manufacturing such products in a minimum interruption of production time period.

The present invention aims to solve the technical problem of providing easy cleaning and/or sterilizing operations or devices for the production of products under inert atmosphere, and/or sterile and/or pyrogen free products, and notably medical, chemical, biochemical, pharmaceutical, electronic, or food products or devices.

Moreover the invention aims to solve the new technical problem of providing a disposable equipment and process enabling to manufacture or package products.

The invention aims to diminish the time of contact of a product or device to be handled, manufactured or packaged, with contaminants or pollutants. The invention aims to avoid the contact of a product or device to be handled, manufactured or packaged, with contaminants or pollutants

DESCRIPTION OF THE INVENTION

The present invention relates to a closed disposable equipment comprising at least two separate disposable isolators including a first disposable isolator and a last disposable isolator, wherein said separate disposable isolator is connected to at least one other separate disposable isolator by at least one connecting means, wherein each separate disposable isolator comprises a working place, said working place being located inside said separate disposable isolator, said working place being under inert atmosphere, and/or disinfected, and/or sterile and/or pyrogen free conditions, said working place enabling the manipulation of containers, products or devices, wherein said closed disposable equipment comprises at least one inlet for introducing containers, products or devices into said closed disposable equipment and at least one outlet for discharging said containers, products or devices from said closed disposable equipment. This closed disposable equipment represents a closed disposable production line.

Each separate disposable device comprises a working place. This working place is located inside said separate disposable device. The term "product" encompasses all type of products, i.e. chemical reagents, substances, or compositions, and devices, i.e. medical devices, electronic devices, containers, etc. Containers encompass vials, trays of vials or containers.

The working places may be directed to handling of product, transferring a product to another place, chemically treating or reacting the product with the products or reagents, physically treating the product, measuring properties of the product, stoppering containers with plugs, capping containers with caps, or packaging the product. In the present invention, it is referred to as "manipulating" or "processing" the product. All these operations may be performed in one or more working places of the disposable production line. One advantage of the present invention is that all these operations may be performed under inert atmosphere, and/or disinfected, and/or sterile and/or pyrogen free conditions.

In one embodiment, the working places of the separate disposable devices have the same purpose. According to another embodiment, working places of the separate disposable devices have different purposes.

In an advantageous embodiment the disposable device or the working place comprises an inert atmosphere and/or is sterile and/or pyrogen free prior to the connection of the disposable production line, i.e. to another disposable device.

Preferably, all of the disposable devices of the production line or the working places thereof comprise an inert atmosphere and/or are disinfected, and/or sterile and/or pyrogen free prior to their connection to the production line.

In one embodiment, all of the disposable devices or working places are kept sterile and/or pyrogen free and/or with an inert atmosphere during the whole time of use in the production line. The invention relates also to production line under inert atmosphere, and/or disinfected, and/or sterile, and/or pyrogen free conditions. In one particular embodiment the invention relates to a sterile and/or pyrogen free production line. Such a production line is a production line where the products are never in contact with non inert atmosphere, and/or non-disinfected, and/or non-sterile, and/or non-pyrogen free conditions.

According to the invention a disposable device is a disposable isolator. Thus the terms "disposable device" may be replaced by the terms "disposable isolator" in the present text. "Isolator" means a device wherein at least the working place is kept sterile and/or pyrogen free and/or with an inert atmosphere.

A typical separable disposable isolator according to the invention may be an inflatable bag comprising a membrane or film wall (usually a plastic film or membrane), wherein one or more containers may be placed inside the bag, and wherein said one or more containers may be introduced into or discharged out from said bag via inlet or outlet means. Said inlet and/or outlet means may be connected to an inlet and/or outlet from another separable disposable isolator. In one embodiment said separable disposable isolator comprises inert atmosphere and/or is sterile and/or pyrogen free. The plastic wall comprises optionally an integrated structure or not to provide a particular shape to the isolator.

For example the production line of the invention comprises 2, 3, 4, 5, 6, 7, 8, 9, or 10 separate disposable isolators each connected to at least one another separate disposable isolator. Therefore, the disposable isolator are connected each others so that they design a closed production line. No particular limitation is made to the number of separate disposable isolators present in the production line. A separate disposable device of the invention comprises one or more connecting means to connect said separate disposable device to at least one another separate disposable device of the disposable production line.

"Connected each others" means either connected to all of the other separate disposable devices or to at least one another separate disposable device. The connection is a parallel-type connection or series-type connection or a parallel-type and series-type connection. A "parallel-type connection" is a connection of one separate disposable device comprising at least two connecting means to another separate disposable device by at least two connecting means. A "series-type connection" is a connection of one separate disposable device comprising at least two connecting means to two other separate disposable devices. A "parallel-type and series-type connection" is for example a connection of one separate disposable device comprising at least three connecting means to second separate disposable device by at least two connecting means and to a third separate disposable device by one connecting means.

The connection between the separable disposable devices is performed using an inlet and/or outlet which comprises a hole or sleeve allowing the passage of at least one or more trays, containers or vials. The inlet and/or outlet may allow the passage of other materials such as chemical products, or reagents or instruments. Typically the hole or sleeve has a cylindrical or rectangular section. One or more trays or vials or containers may be introduced inside a separate disposable isolator via an inlet, such as a sleeve. Said inlet has a proper dimension to permit the trays, vials or containers to be introduced inside the disposable isolator. Typical dimensions of the transversal section of the connecting means are from 0.5 cm to 2 m for each side or diameter. Preferably the wider side is of at least 15 cm to allow an easy transfer of the products, devices, or containers. These dimensions are not limiting the invention. In particular the inlet and/or outlet may be of a broader size if the production line of the invention is used at a large industrial scale.

Said inlet or outlet means may be sealed by a clamp. Said clamp may be automatically opened or closed by pneumatic means, optionally controlled by a computer. This closing should be sufficient to keep the disposable isolator disinfected, sterile or depyrogenated.

The same applies to the outlet means for discharging said products, devices, or containers.

Typically, an outlet of a separate disposable device is connected to an inlet of another separate disposable device.

Said inlet or outlet means may be sealed or closed by a closing means. A type of closing means is a clamp. Said closing means may be manually opened or closed, or automatically opened or closed, such as by a pneumatic means, optionally controlled by a computer. This closing should be sufficient to keep the disposable isolator disinfected, and/or sterile, and/or depyrogenated, and/or under inert atmosphere.

A production line is typically a set of sequential operations established in a factory or operating room whereby materials are put through a refining process to produce an end-product or a resulting product; or whereby components are assembled to make a finished article.

Typically, raw materials such as medical, chemical, biochemical or pharmaceutical, or food products require a sequence of treatments to render them useful. Typically, this requires controlling the quality of raw materials, pre-treatment of raw materials, physically treating and/or chemically reacting raw materials, controlling the quality of resulting materials, packaging the resulting materials.

The present invention is not limited to human intervention and covers robot manipulation.

By "robot manipulation", it is understand any automatic means helping the manipulation, but not excluding human intervention. This manipulation may be driven by a computer or any control system.

Said separate disposable isolator may be a one piece device, preferably made of at least one disposable material such as plastics, as for example PE (Polyethylene), PP (Polypropylene), PFA (Perfluoroalkoxy), polyaryletherketone, PEEK (Poly(ether ether ketone), etc. Typically this is HDPE/Tyvek® bag. This bag may be produced in ISO Class 5 environment and ultraclean to level 200 (according to IEST-STD-CC1246D). This isolator may be prepared by combining different materials easily recycled and known generally as disposable materials. A preferred embodiment relates to a disposable isolator made entirely of one or more transparent materials, but translucent materials may be used. Another embodiment relates to a transparent or translucent disposable isolator. No particular limitation is made on the material of the invention, knowing that it aims to be easily disposed of, or a reusable or valuable waste and usable according to the goal of the production line. A preferred embodiment relates to flexible materials since they give reduce the place of the disposable isolator and makes it easy to store and to dispose of.

The invention relates in particular to a production line comprising at least one disposable isolator described in the European Patent application n°EP 09305210.8 filed on Mar. 6, 2009 in the name of Disposable-Lab which is incorporated herein by reference in its entirety.

In one embodiment at least one of the separate disposable isolators of the production line comprises a top portion and a bottom portion, said top and bottom portions being linked together by one or more side walls forming all together an inside portion, wherein said bottom portion comprises at least one support area for positioning at least one container, wherein said disposable isolator comprises at least one filling means,
wherein said filling means and said support area cooperating, independently or not, to position at least one container substantially in front of said filling means to fill said container by a product.

According to one embodiment, said bottom portion comprises at least one support area comprising an outside surface and an inside surface, wherein said outside surface is defining a receiving means to receive a support means to support at least one container, said support means is located outside said disposable isolator, said inside surface is defining a receiving means to receive at least one container located inside said disposable isolator, and wherein said container is moved using said support means, said disposable isolator comprises at least one filling means located in the top portion, said filling means being substantially in front of said support area.

The support area of said device may comprise a plane or substantially plane surface and flexible side parts. The plane surface may present rigid parts or may be fully rigid. This surface is designed to receive one or more containers. In an embodiment the plane surface is designed to receive a well plate or a tray comprising several containers or vials. Such trays or well plates are marketed for example by Newmark system Inc. A plane surface may include a rigid plastic material surface thermosealed, or fixed by other means, to the flexible material of the disposable isolator support area. The support area is designed to receive a support means, such as a XY or XYZ plate, and allows its movement, said support means being located outside said disposable isolator.

In an embodiment, the filling means comprises at least one needle for filling a container by a product, said needle being preferentially fixed on the disposable isolator. Without any particular limitation to any way to fix said needle, the needle may be sealed, notably thermosealed, screwed, clipped, or clamped. The goal is that said needle is sufficiently hermetically and/or watertight fixed, attached or locked to the disposable isolator. Pre-filled syringes may be used to add one or more products. Such syringes are marketed by BD for pre-filled syringes. The filling means may move upwards and/or downwards to fill a container. For allowing a movement of said filling means, the internal pressure of the disposable isolator may vary. The pressure of structure supporting means may vary too, separately or at the same time. When decreasing the pressure the filling means goes downwards, and the contrary when pressure is increased. The disposable isolator may comprise means for controlling the pressure, and/or means for varying the pressure of inside part of said isolator. A special gas may be injected near the filling means to create a specific gas environment during injection of the fluid filling the containers. Typically this special gas may be an inert gas.

A filling means is fully described in WO 2007/019568 (US 2007/0034643), which is incorporated by reference in its entirety. Said filling means is a volumetric fluid dispensing device of a predetermined volume of fluid to fill the containers.

A disposable isolator is typically a bag, wherein one or more containers may be placed inside the bag, and wherein a support for these containers is located outside said bag. In one embodiment said support means may move the location of the containers inside the bag, notably to position at least one container in front of a filling means so that one or more containers may be filled by one or more products. In another embodiment, said filling means may move notably to be positioned in front of at least one container so that one or more containers may be filled by one or more products.

In one embodiment, one or more, but preferably all disposable isolators are gamma-rays sterilized.

A disposable isolator of the invention is substantially flexible so it may be easily disposed of. The isolator is made of one or more flexible materials. The upper and bottom portions, and side walls may be made of the same or different materials.

A flexible part of a disposable isolator may comprise one or more rigid parts.

A disposable isolator may be supported or hanged by a rigid support or casing. The disposable isolator may be inflated. In order to present a particular shape, the isolator may comprise one or more structure forming means which may be inflated separately from or together with the inside portion. These structure forming means may comprise one or more tubes, casing, or housing. This particular shape may vary and/or be controlled by the pressure of the inside portion of the disposable isolator or the pressure of said structure forming means.

The container may be a plurality of containers or vials advantageously placed into a tray, and having a position which may optionally be determined by an automatic calculator or any other means.

The pressure of a disposable isolator inside portion may be fixed or vary. The inside portion pressure may be higher than the pressure of the pressure outside of said isolator, or lower. For example, such isolator inside pressure is of 10-50 mbar higher than the outside pressure, or of 1-20 mbar lower than the outside pressure.

The bottom portion of said isolator comprises one or more other areas designed to receive other means. In an embodiment an area is designed to receive a weight scale and preferably an analytical balance. This area may be made completely or partially of a flexible material. If a weight scale is to be used, it is preferred that said flexible material allows the positioning of said weight scale and do not impact the weight measure. This area may present a plane surface flexible and thin enough to be positioned correctly on a weight scale or analytical balance and avoid measure errors. This may be a film of PE, polysulfone, etc. This area may comprise on the outside surface one or more means for locking said support means (such as a XYZ or XY plate) and/or comprising on the inside surface one or more means for locking said container.

A disposable isolator may comprise at least one means for manipulating a product or material introduced inside said disposable isolator. This may be one or more pairs of gloves. In one embodiment, one or more, optionally all, separate disposable isolators comprise at least one pair of gloves.

The production line or disposable equipment avoids any contamination by external pollutants of the product(s) filling a container. The products or devices added according to the invention remain protected by the internal atmosphere and/or conditions starting from the filling means to the container until there sealing. Therefore, it is referred to a closed disposable equipment.

There is no limitation on the products filling said container. These are solids, such as powders, fluids such as gas or liquids, such as mono or multiphasic liquids, all type of solutions, suspension or emulsions. These products may be pharmaceutical, veterinary or cosmetics compounds, biohazardous or potent compounds, anti-cancer or anti-viral drugs, etc.

In an embodiment an inert fluid is used as internal atmosphere of said isolator. Such fluid may be or comprise nitrogen, helium, argon, neon, krypton or oxygen or any other suitable liquefiable gas. Usually nitrogen is used as inert fluid. Usually before filling a container or vial by a product, a step of filling said container or vial by an inert fluid is required.

Using such an inert fluid as internal atmosphere inside the isolator avoids this step of filling the containers by an inert fluid.

The disposable isolator may comprise means for receiving one or more probes and/or sensors, without any limitation to particular probes or sensors. Sensors may be temperature, pressure, p(O2), or p(N2) sensors, or alarm devices. These sensors or probes may be connected to or controlled by a computer. Information may be exchanged between a sensor or probe and a computer. Controlling the pressure may be important to check for any possible leak. An alarm may inform of a leak, and thus of a small hole in the isolator.

The invention avoids using a laminar flow to protect the product from a contamination. No such laminar flow is needed because the product is safely protected inside the disposable isolator.

The containers or vials may be protected when located inside a tray by placing a removable sheet onto the upper surface of the tray. For example this may be a plastic removable sheet opened after the tray is put inside the disposable isolator. The same may be used to package and protect other devices or products.

The production line of the invention may be maintained in the proper shape by inflation during the manipulation or manufacturing process. Each disposable isolator may be inflated or may comprise structure forming means to maintain them in a proper shape or design.

The invention further relates to a method for preparing a closed disposable production line, said method being as follows:

- Deflated disposable isolators are positioned on one or more laboratory tables, on the ground, or hung, partially or entirely;
- Inflating said disposable isolators;
- After inflation an integrity test is preferably performed;
- All disposable isolators of the production line are connected according to the design of the closed production line;
- Each separate disposable isolator is preferably sterilized;
- One or more, and preferably all, closing means of the connections between isolators are opened;
- Preferably a test is performed to ensure the proper pressure is maintained in the closed production line;
- The closed production line is prepared.

The disposable isolators and/or structure forming means may be inflated separately or together. The structure forming means may be inflated only. A 0.22 micron filter is preferably used to inflate with air or nitrogen the separate disposable isolators. The disposable isolator(s) may present a higher or lower pressure than the laboratory pressure. Each separate disposable isolator is preferably sterilized for example via VHP means.

After these steps, a container, product, or device may be introduced through the inlet, which is generally a sleeve, and said container, product, or device being positioned on a support area inner surface. Preferably this surface is rigid to correctly and easily position the container, product, or device and the support means.

If the containers do not contain any product or should contain at least one more product, the containers may be filled inside a disposable isolator for filling said container with the required product(s), for example using a disposable isolator as described in EP 09305210.8.

After the filling steps, the container, product, or device may be discharged through the outlet means, which is generally a sleeve. Inlet and outlet may be hermetically and/or watertight closed by any suitable means, typically by clamps optionally using seals. Inlet and outlet are opened only when needed.

The containers may thus be transferred to another disposable isolator for a subsequent step in the production line.

A disposable isolator may comprise a casing including one or more areas for fixing or locking external devices. The casing may be a plastic sheet comprising one or more holes designed to receive said external devices. External devices may be selected from the group consisting of the above described support area, the above described inlet, the above described outlet, the above described filling means, the above described manipulation means, and other areas such as area designed to receive a weight scale or an analytical balance, or a pre-filled plastic bag. Pre-filled plastic bag are plastic bag containing one or more products or devices under the invention required atmosphere and/or conditions. Such pre-filled plastic bags are manufactured by ATMI, such as for example contained Powder Transfer Bag (cPTB) marketed as Newsafe™. The disposable isolators according to the invention may be marketed without or with some of the external devices. Said external devices may be marketed separately from the isolator casing.

A disposable production line may comprise a separate disposable isolator as described in the European Patent application n°EP 09305483.1 filed on May 5, 2009 in the name of Disposable-Lab which is incorporated herein by reference in its entirety. In particular said isolator is an apparatus comprising a chamber for physically and/or chemically treating one or more samples or products, said apparatus comprising a door for introducing samples inside the apparatus chamber or bringing samples outside the apparatus, said apparatus comprising a membrane or film defining a chamber wall inside said apparatus when the door is closed, and wherein said membrane or film comprises an inlet and an outlet for vials or containers for locating one or more vials or containers inside said chamber. This apparatus is advantageously selected from the group consisting of an oven, a drying equipment, a dryer, a freeze-dryer, an autoclave, a sterilizer, a gas chamber (for example for cold gas sterilization such as $H_2O_2$ or ethylene oxide sterilization), and a depyrogenation apparatus. The membrane or film advantageously comprises an inlet and an outlet for vials or containers for locating one or more vials or containers inside said chamber or discharging these vials or containers. This inlet/outlet is typically a sleeve which is connected to another disposable isolator of the production line. This inlet/outlet may be closed or sealed by closing means. A typical closing means is a clamp optionally with one or more seals. This closing should be sufficient to keep the disposable isolator disinfected, and/or sterile, and/or depyrogenated, and/or under inert atmosphere.

According to one embodiment, a disposable isolator of the invention is a disinfected, sterile or depyrogenated area to perform at least one of the following steps: handling of at least one container, transferring a container to another area, chemically treating or reacting a product contained in a container with one or more products or reagents, physically treating a product contained in a container, measuring properties of the product contained in a container, or packaging one or more containers. Containers refer also to trays, syringes, or vials, notably for the pharmaceutical, chemical, or cosmetic industry. Containers may be replaced by pieces of a device to assembly, such as for example an electronic device or a medical device.

The production line may comprise one or more disposable isolators such as an isolator containing sterile and depyrogenated containers packaged in a sterile and depyrogenated packaging, an isolator to take off sterile and depyrogenated containers packaged from a sterile and depyrogenated packaging, an isolator to weight the products, a filling isolator to fill one or more containers with one or more products, an isolator for stoppering the containers with plugs, an isolator for capping the containers, an isolator to package the containers. Stoppering systems, such as Lyoseal™, are manufactured for example by Biocorp.

According to one embodiment the production line comprises a series-type connection of (a) an isolator containing sterile and depyrogenated containers packaged in a sterile and depyrogenated packaging, (b) an isolator to take off sterile and depyrogenated containers packaged from a sterile and depyrogenated packaging, (c) a filling isolator to fill one or more containers with one or more products, (d) an isolator for stoppering the containers with plugs, and of (e) an isolator for capping the containers. In one embodiment, said filling isolator is one described in EP 09305210.8. This type of production line configuration is particularly adapted to liquid products.

According to one embodiment, said filling isolator comprises a parallel connection to one or more mixing isolators. A mixing isolator is typically a plastic bag comprising an agitator system. An agitator system particularly designed for the mixing in disposable bags is described in EP 0951895 filed on Mar. 24, 2009 in the name of Jean-Pascal Zambaux. Other agitating systems which may be used according to the invention are manufactured by ATMI, such as Newmix-LevTech™ disposable mixers. Millipore and Facturus are also marketing other mixing systems.

According to one embodiment the production line comprises a series-type connection of (a) an isolator to weight the products, (b) a filling isolator, and (c) an isolator to package the containers. This type of production line configuration is particularly adapted to powder or solid products. Solid products may be aggregated or compact powder products such as tablets, or capsules, or dose (sachet or bag) of powder products. Isolators may be connected via a device as described in the French patent application n° FR 08 54131 to CHANGEXPLORER incorporated by reference. Such a device may be connected via one or more clamps and/or screws. The transfer between isolators may be performed using a device described in FR 08 54131. This particular device may be used to make a proper diffusion of the Vaporized Hydrogen Peroxide (VHP) in all embodiments. This enables sterilizing the connexion between 2 isolators. In a particular embodiment where transfer of powders is needed; this particular device enables notably to avoid the presence of powder in the connection between two isolators.

According to one embodiment, the production line comprises a parallel-type and series-type connection of (a) an isolator comprising one or more type of devices to be assembled packaged under sterile and pyrogen free conditions, typically for manufacturing a medical device, (b) an isolator for assembling said device(s), (c) an isolator for packaging said assembled device(s) under sterile and pyrogen free conditions, and (d) optionally an isolator comprising containers already manipulated or processed through another part of the production line.

According to one embodiment, the connection between the separate disposable isolators comprises a connecting device. According to one embodiment, said connecting device comprises a cylindrical shape comprising a proximal end and a distal end, said proximal end comprising connecting means for connecting said proximal end to a first separable disposable isolator, said distal end comprising connecting means for connecting said distal end to a second separable disposable isolator. In one embodiment, said connecting device comprises a Vaporized Hydrogen Peroxide (VHP) system to sterilise the connecting device.

The invention relates to a method for manipulating (processing or manufacturing) products under disinfected, and/or sterile, and/or depyrogenated, conditions, and/or under inert atmosphere, wherein said products are going through a closed production line under disinfected, and/or sterile, and/or depyrogenated, conditions, and/or under inert atmosphere, by introducing said products into the closed production line via an inlet of a first disposable isolator, manipulating said products inside said closed production line, and discharging the manipulated products from the closed production line via an outlet of a last disposable isolator.

The invention further relates to a method for packaging disinfected, sterile and/or depyrogened products, wherein said method comprises introducing disinfected, sterile and/or depyrogened products in the production line, manipulating the products to perform one or more operations and discharging the disinfected, sterile and/or depyrogened packaged products from the production line. In one embodiment, products are going through a first disposable isolator of the disposable production line to a last disposable isolator.

Advantageously, in a production line comprising multiple disposable isolators, said multiple disposable isolators comprising an upstream isolator, a downstream isolator, and optionally one or more subsequent downstream isolator, each isolator comprising inlet and outlet sleeves, wherein sleeves of said upstream isolator are connected to sleeves of one or more downstream isolators, the method of the invention comprises:

a—Isolating each isolator from other isolators to which it is connected by closing sleeves using closing means;
b—Opening a closing means closing upstream isolator inlet sleeve;
c—Introducing products inside said upstream isolator;
d—Closing said closing means closing upstream isolator inlet sleeve;
e—Manipulating said products inside said upstream isolator;
f—Opening a closing means closing upstream isolator outlet sleeve;
g—Opening a closing means closing a first downstream isolator inlet sleeve;
h—Transferring products from upstream isolator to said first downstream isolator;
i—Closing said closing means closing said upstream isolator inlet sleeve;
j—Manipulating said products inside said first downstream isolator;
k—Opening a closing means closing said first downstream isolator outlet sleeve;
l—Discharging said products from said first downstream isolator;
m—Closing said closing means closing said first downstream isolator outlet sleeve;
n—Optionally, repeating steps a- to n- to transfer said products to one or more subsequent downstream isolators.

For any subsequent transfer of the products, said first downstream isolator is referred to as an upstream isolator and a subsequent isolator as a downstream isolator.

"Upstream" and "downstream" refer to the flow of the products in the production line. Products enter the disposable production line through an upstream isolator and go through downstream isolator(s) to process or manipulate the products inside said disposable production line. Products refer to devices, containers or chemical products.

"Process" and "manipulate" refer to the handling of product, transferring a product to another place, chemically treating or reacting the product with the products or reagents, physically treating the product, measuring properties of the product, or packaging the product.

Advantageously, for transferring containers from an upstream isolator to a first or subsequent downstream isolator via a connecting device comprising a proximal end and a distal end, said proximal end comprising connecting means for connecting said proximal end to an upstream isolator, said distal end comprising connecting means for connecting said distal end to a downstream isolator, the method of the invention comprises the following steps:

Processing according to steps a- to f- according to the above description;
Processing as follows:
h1—Transferring containers from upstream isolator to said connecting device;
h2—Closing said closing means closing said first upstream isolator outlet,
h3—Opening a closing means closing said first downstream isolator inlet sleeve;
h3—Transferring containers from connecting device to said first downstream isolator;
h4—Closing said closing means closing said first downstream isolator inlet sleeve;
Processing according to steps j- to n-.

In another embodiment, in a production line comprising multiple disposable isolators, said multiple disposable isolators comprising an upstream isolator, a downstream isolator, and optionally one or more subsequent downstream isolator, each isolator comprising inlet and outlet sleeves, wherein sleeves of said upstream isolator are connected to sleeves of one or more downstream isolators, the method of the invention comprises:

a—Isolating each isolator from other isolators to which it is connected by closing sleeves using closing means;
b—Opening all closing means except the first upstream isolator inlet sleeve and the last downstream isolator outlet sleeve;
c—Opening said first upstream isolator inlet sleeve;
d—Introducing products inside said upstream isolator;
e—Closing said first upstream isolator inlet sleeve;
f—Manipulating said products inside said production line;
g—Opening said last downstream isolator outlet sleeve;
h—Discharging said products from said last downstream isolator;
i—Closing said last downstream isolator outlet sleeve.

The invention further relates to a method for preparing sterile and pyrogen free trays of containers or vials comprising a liquid (for example a cartridge for a prefilled-syringe), said trays being processed though a disposable production line of the invention.

The invention further relates to a method for preparing sterile and pyrogen free trays of containers or vials comprising a powder (for example a freeze-dried powder), said trays being processed though a disposable production line of the invention.

The invention further relates to a method for preparing sterile and pyrogen free medical devices (for example a syringe or a prefilled-syringe), said medical device being processed though a disposable production line of the invention.

After using the production line, it may be disposed of. The last isolator containing the manipulated or packaged products, that is to say the end product, is disconnected from the production line after closing all inlets and outlet from said last isolator. Preferably a test of the proper pressure is performed before deflating the production line. This is typically an integrity test as know in the art. After deflation of the disposable production line, the deflated production line is packaged as a waste product. These wastes are preferably decontaminated by VHP or an autoclave step if necessary.

On the drawings

FIG. 2 represents a schematic representation of a second embodiment of the invention;

FIG. 3 represents a schematic representation of a third embodiment of the invention;

Other aims, characteristics and advantages of the invention will appear clearly to the person skilled in the art upon reading the explanatory description which makes reference to the figures which are given simply as an illustration and which in no way limit the scope of the invention.

The figures make up an integral part of the present invention, and any characteristic which appears novel with respect to any prior state of the art from the description taken in its entirety, including the figures, makes up an integral part of the invention in its function and in its generality.

Thus, every figure has a general scope.

Figure 1:
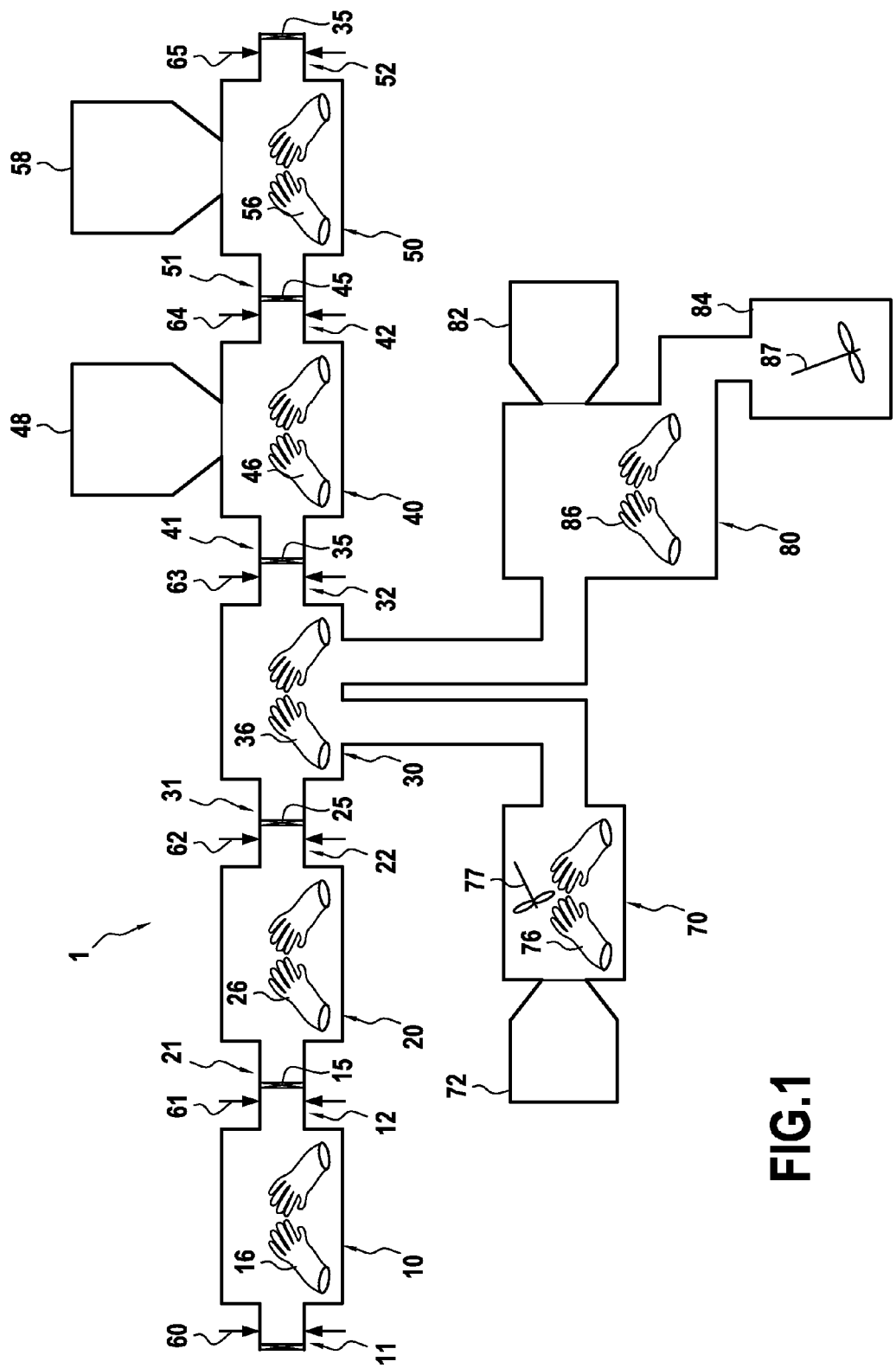
FIG. 1 represents a schematic representation of a first embodiment of the invention.

FIG. 1 represents a production line (1) for packaging for example liquid products under sterile and pyrogen free conditions, said production line comprising a series-type connection of an isolator (10) containing sterile and depyrogenated containers packaged in a sterile and depyrogenated packaging connected to an isolator (20) to take off sterile and depyrogenated containers packaged from a sterile and depyrogenated packaging, said isolator (20) being connected to a filling isolator (30) to fill one or more containers with one or more products, said filling isolator (30) being connected to isolator (40) for stoppering the containers with plugs, and said isolator (40) being connected to an isolator (50) for capping the containers. In one embodiment, said filling isolator (30) is one described in EP 09305210.8. The disposable isolator (10, 20, 30, 40, 50) may be connected via connecting means (15, 25, 35, 45). Inlets and outlets of isolators are represented here by sleeves extending from one isolator (upstream isolator) to another isolator (downstream isolator). Thus, said connecting means may connect an outlet (12, 22 32 42) of an upstream isolator to an inlet (21, 31 41 51) of a downstream isolator. The products may be introduced in the first isolator (10) via inlet (11) of the first isolator (10) of the production line (1) and may be discharged via outlet (52) of the last isolator (50). Schematic arrows perpendicular to the connecting means schematically represent closing means (60, 61, 62, 63, 64, 65) which may close the passage between to isolators. According to one embodiment, said closing means should normally be opened only when products or device are transferred from one isolator to another. According to another embodiment, closing means (61, 62, 63, 64) are opened while processing or manipulating the products or containers inside said production line. According to this embodiment closing means (61) are only opened to introduce the products or containers into the production line, and closing means (65) are only opened to discharge the products or containers from the production line. Each isolator (10, 20, 30, 40, 50) may comprise at least one pair of gloves (16, 26, 36, 46, 56) to manipulate the products or devices from the exterior. Optionally said filling isolator is connected in parallel-type connection to a disposable mixing isolator (70, 80), said mixing isolator (70, 80) comprising an impeller (77, 87), optionally a pair of gloves (76, 86) and optionally a side pre-filled transfer bag (72, 82) for adding products into said mixing isolator (70, 80). Mixing isolator (70) is preferred for small volumes (generally up to 5 litres) and mixing isolator (80) is preferred for larger industrial scale (generally from 5 to 200 litres).

FIG. 2 represents a production line (2) for packaging for example powdery products under sterile and pyrogen free conditions, said production line comprising a series-type connection of an isolator (210) containing sterile and depyrogenated products (217) packaged in a sterile and depyrogenated packaging, said isolator (210) being connected to an isolator (220) to discharge the products (217) from their packaging, to weight the products (217), and to filling the products (217) into containers (227), said isolator (220) being connected to an isolator to package the containers (227). This type of production line configuration is particularly adapted to powder or solid products, particularly when two or more products should be mixed before packaging. Solid end products may be aggregated or compact powder products such as tablets, or capsules, or dose (sachet or bag) of powder products. Said packaged products (217) are for example transferred from a transfer bag (212). Said isolator (210) comprises means for agitating said product (217). Each isolator (210, 220, 230) may comprise at least one pair of gloves (216, 226, 236) to manipulate the products or devices from the exterior. The disposable isolator (210, 220, 230) may be connected via connecting means (215, 225). Schematic arrows perpendicular to the connecting means schematically represent closing means (260, 261, 262) which may close the passage between to isolators. Closing means may be opened and closed as described with reference to FIG. 1.

FIG. 3 represents a production line 3, typically for manufacturing a medical device, said production line comprising a parallel-type and series-type connection of an isolator (350) comprising one or more type of pieces of devices to be assembled packaged under sterile and pyrogen free conditions, an isolator (360) comprising one or more type of pieces of devices to be assembled packaged under sterile and pyrogen free conditions, said isolator (360) and isolator (350) being connected to an isolator (370) for assembling said pieces of devices, said isolator (370) being connected to an isolator (380) for packaging said assembled devices under sterile and pyrogen free conditions. Optionally said isolator (350) comprises products, devices, or containers to be assembled to piece of device from isolator (360), said products, devices, or containers from isolator (350) being prepared by manipulation or processing from another part of the production line. Said isolator (350) optionally comprises a transfer bag (357) for capping containers. Typically isolator (350) comprises cartridge for syringe, said cartridge being filled with a product according to FIG. 1 and capped in isolator (50, 350). The syringes to which the cartridges should be added are coming from isolator (360), and prefilled-syringes are assembled in isolator (370), then packaged in isolator (380). Each isolator (350, 360, 370, 380) may comprise at least one pair of gloves (356, 366, 376, 386) to manipulate the products or devices from the exterior. The disposable isolator (350, 360, 370, 380) may be connected via connecting means (355, 365, 375). Schematic arrows perpendicular to the connecting means schematically represent closing means (360, 361, 362, 363, 364) which may close the passage between to isolators. Closing means may be opened and closed as described with reference to FIG. 1.

Figure 4:
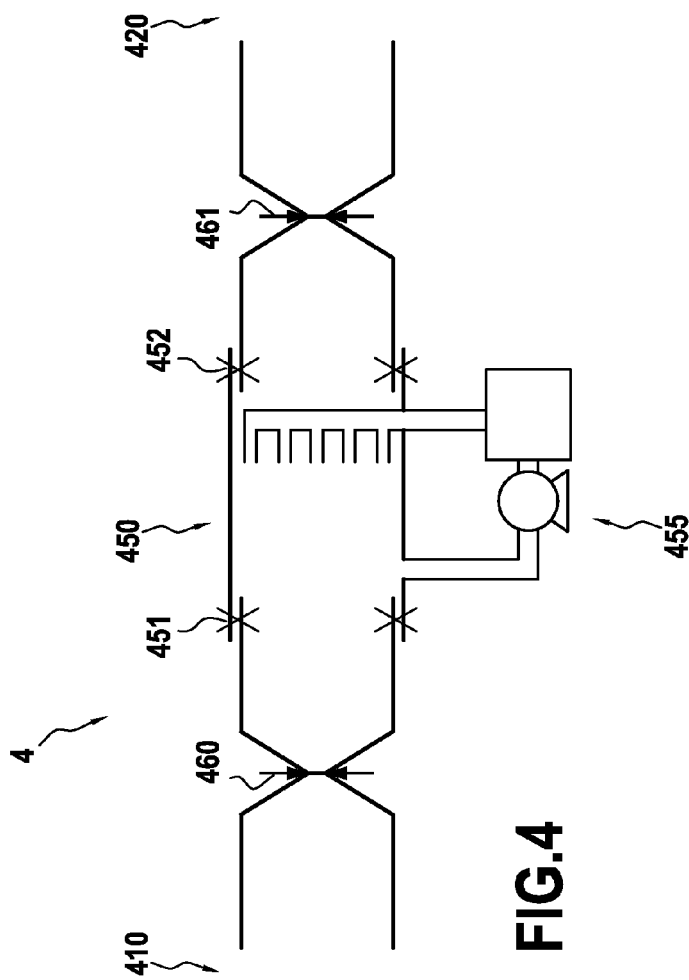
FIG. 4 represents a schematic perspective of a connecting device connecting an upstream and a downstream isolator.

FIG. 4 represents a connecting device (450) having a cylindrical shape and comprising a proximal end and a distal end, said proximal end comprising connecting means (451) for connecting said proximal end to a first separable disposable isolator (410), said distal end comprising connecting means (452) for connecting said distal end to a second separable disposable isolator (420). In one embodiment, said connecting device comprises a Vaporized Hydrogen Peroxide (VHP) system (455) to sterilise the connecting device. Said Vaporized Hydrogen Peroxide (VHP) system (455) comprises circulating means and injection means for H2O2. Schematic arrows perpendicular to the connecting means schematically represent closing means (460, 461). In one embodiment, the connecting device is one described in FR 08 54131 to CHANGEXPLORER. By injecting VHP, this device enables sterilizing the connection between two isolators.

Figure 5:
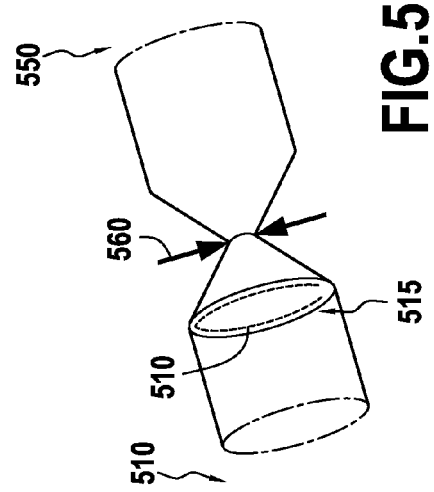
FIG. 5 represents a schematic perspective of a section of an extremity of a sleeve of a disposable isolator.

FIG. 5 represents a schematic perspective of a section of an extremity of a sleeve of a disposable isolator (510) connected to an isolator or a connecting device (550), said extremity comprising a pre-cut membrane (512). Said pre-cut membrane (512) may be opened after connection to an isolator or a connecting device and optionally after sterilization. Said opening is performed by pushing, pulling, or pressing the pre-cut membrane (512) along the pre-cut (515). Closing means (560) may be positioned before or after said pre-cut membrane (512).

The invention claimed is:

1. A closed production line comprising multiple disposable isolators, said multiple disposable isolators comprising an upstream isolator, and a downstream isolator, each isolator comprising an inflatable bag with at least one pair of gloves attached thereto, said isolators further comprising inlet and outlet sleeves, wherein the inlet or outlet sleeves of said upstream isolator are connected to one or more downstream isolators.

2. The closed production line of claim 1, wherein said each disposable isolator comprises an integrated structure providing a particular shape to each separable disposable isolator.

3. The closed production line of claim 1, wherein at least one of said inlet or outlet sleeves is sealed or closed by a closure.

4. The closed production line of claim 1, wherein each said disposable isolator is a disinfected, sterile or depyrogenated area.

5. The closed production line of claim 1, wherein at least one of said inlet or outlet sleeves comprises a cylindrical shape comprising a proximal end and a distal end, said proximal end adapted for connecting said proximal end to the upstream isolator, said distal end adapted for connecting said distal end to the downstream isolator.

6. The closed production line of claim 1, wherein at least one of said sleeves includes a Vaporized Hydrogen Peroxide (VHP) system for providing sterlization.

7. A closed disposable equipment for processing a product, comprising:
a first disposable isolator and a second disposable isolator connected to the first disposable isolator by at least one connector, wherein each disposable isolator comprises an inflatable bag comprising a membrane or film wall, and wherein each disposable isolator further comprises a working place, said working place being located inside said disposable isolator, said working place being under inert atmosphere, disinfected, sterile, and pyrogen free, said working place enabling the manipulation of the product, wherein each said disposable isolator comprises an inlet for receiving the product into the working place and an outlet delivering the product from the working place, and further including at least one clamp for closing at least one of the inlets or outlets.

8. The apparatus of claim 7, wherein at least one of the isolators comprises means for filling at least one product.

9. The apparatus of claim 8, wherein the means for filling comprises a syringe.

10. The apparatus of claim 8, wherein the means for filling comprises a needle.

11. The apparatus of claim 8, wherein at least one of the isolators comprises an agitator.

12. An apparatus for providing a production line for processing one or more products, comprising:
   first and second disposable isolators, each including an inlet adapted for receiving the product in an interior compartment and an outlet for delivering the product from the interior compartment;
   a first flexible sleeve for connecting to the inlet of each isolator;
   a second flexible sleeve for connecting to the outlet of each isolator; and
   a clamp for closing at least one of the inlets or outlets.

13. The apparatus of claim 12, wherein each of said isolators comprises a flexible bag.

14. The apparatus of claim 12, wherein the first flexible sleeve connected to the outlet of the first isolator is connected to the second flexible sleeve connected to the inlet of the second isolator.

15. The apparatus of claim 14, wherein each isolator comprises a working place, said working place being under inert atmosphere, and/or disinfected, and/or sterile and/or pyrogen free conditions.

16. The apparatus of claim 13, wherein the flexible bag comprises at least one pair of gloves attached thereto.

17. The apparatus of claim 12, wherein the damp comprises a pneumatic means for automatically opening and closing the clamp.

18. The apparatus of claim 17, further including a controller for controlling the pneumatic means.

* * * * *